United States Patent [19]
Heeres et al.

[11] Patent Number: 5,998,413
[45] Date of Patent: Dec. 7, 1999

[54] ITRACONAZOLE AND STEREOISOMERS

[75] Inventors: Jan Heeres, Vosselaar; Jean Louis Mesens, Wechelderzande; Jozef Peeters, Beerse, all of Belgium

[73] Assignee: Janssen Pharmaceutica, N.V., Belgium

[21] Appl. No.: 08/676,531

[22] Filed: Jul. 9, 1996

Related U.S. Application Data

[63] Continuation of application No. 08/295,885, filed as application No. PCT/EP93/00522, Mar. 10, 1993, which is a continuation-in-part of application No. 07/853,648, Mar. 18, 1992, abandoned.

[51] Int. Cl.⁶ .................. A61K 31/495; A61K 31/50; C07D 403/14
[52] U.S. Cl. .................. 514/252; 514/384; 544/359; 544/367
[58] Field of Search .................. 514/252, 383, 514/384, 399; 544/350, 367

[56] References Cited

U.S. PATENT DOCUMENTS

| | | | |
|---|---|---|---|
| 4,267,179 | 5/1981 | Heeres et al. | 424/25 D |
| 4,490,530 | 12/1984 | Heeres et al. | 544/370 |
| 4,983,583 | 1/1991 | Bodor | 514/58 |
| 5,002,935 | 3/1991 | Bodor | 514/58 |
| 5,017,566 | 5/1991 | Bodor | 514/58 |
| 5,024,998 | 6/1991 | Bodor | 514/58 |
| 5,214,046 | 5/1993 | Guerry et al. | 514/255 |
| 5,474,997 | 12/1995 | Gray et al. | 514/252 |

FOREIGN PATENT DOCUMENTS

WO 90/11754  1/1990  WIPO.

OTHER PUBLICATIONS

Nerurkar et al. *J. Clin. Pharm.*, vol. 32(10):935–943, (1992). Abstract only.

Hardin, et al., "Pharmacokinetics of Itraconazole following Oral Administration to Normal Volunteers", *Antimicrobial Agents and Chemotherapy*, 32, No. 9, 1988, 1310–1313.

J. Heeres, et al., "Antimycotic Azoles. 7. Synthesis and Antifungal Properties of a Series of Novel Triazol–3–ones", *J. Med. Chem.*, 27, No. 7, 1984, 894–900.

Hostetler, et al., "Effect of cyclodextrin on the pharmacology of antifungal oral azoles", *Antimicrobial Agents and Chemother.*, 36, (2), 1992, 477–480.

Stinson, "Wave of new enantiomer products set to flood the market as chemists develop chiral technology for large–scale production processes", *C&EN*, 71(39), Sep. 27, pp. 38–63.

Stinson, "New single–isomer products on the chiral drug market create demand for enantiomeric intermediates and enantioselective technologies", *C&EN*, 72(38), Sep. 19, 1994, pp. 38–72.

J. Van Cutsem, et al., "Oral and parenteral therapy with saperconazole (R 66905) of invasive aspergillosis in normal and immunocompromised animals", *Antimicrobial Agents and Chemo.*, 33, No. 12, 1989, 2063–2068.

J. Van Cutsem, et al., "Antimycotic Azoles. 7. Synthesis and Antifungal Properties of a Series of Novel Triazol–3–ones", *J. Med. Chem.*, 27, No. 7, 1984, 894–900.

J. Van Cutsem, et al., "In vitro Antifungal Spectrum of Itraconazole and Treatment of Systemic Mycoses with Old and New Antimycotic Agents", *J. Chemother.*, 38, Supp. 1, 1992, 3–11.

*Primary Examiner*—Howard C. Lee
*Attorney, Agent, or Firm*—Woodcock Washburn Kurtz Mackiewicz & Norris LLP

[57] ABSTRACT

Anti-infective compositions for the treatment of a human in need of therapy for a systemic or topical fungal infection which comprise a pharmaceutically acceptable carrier and a therapeutically effective amount of (2R,4S) itraconazole or a pharmaceutically acceptable salt thereof, substantially free of its (2S,4R) stereoisomer.

13 Claims, No Drawings

ITRACONAZOLE AND STEREOISOMERS

This application is a continuation of applicants' U.S. application Ser. No. 08/295,885, filed Jan. 26, 1995, which is a U.S. National Stage application of PCT/EP93/00522, filed Mar. 10, 1993, which is a continuation-in-part of U.S. application Ser. No. 07/853,648, filed Mar. 18, 1992 now abandoned. The entire contents of each aforesaid applications is incorporated by reference herein.

The present invention is concerned with the stereoisomeric forms of itraconazole and saperconazole, processes for preparing said stereoisomeric forms, the complexes thereof with cyclodextrin derivatives, pharmaceutical compositions comprising said complexes and methods of preparing said complexes and pharmaceutical compositions.

Itraconazole or (±)cis-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methyl-propyl)-3H-1,2,4-triazol-3-one, is a broadspectrum antifungal compound developed for oral, parenteral and topical use and is disclosed in U.S. Pat. No. 4,267,179. Its difluoro analog, saperconazole or (±)cis-4-[4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-2,4-dihydro-2-(1-methylpropyl)-3H-1,2,4-triazol-3-one, has improved activity against Aspergillus spp. and is disclosed in U.S. Pat. No. 4,916,134. Both compounds exist as a mixture of four stereoisomers.

The development of efficaceous pharmaceutical compositions of itraconazole and saperconazole is hampered considerably by the fact that said compounds are only very sparingly soluble in water. The solubility of both compounds can be increased by complexation with cyclodextrins or derivatives thereof as described in WO 85/02767 and U.S. Pat. No. 4,764,604.

Unexpectedly, it has now been found that each of the individual stereoisomers of itraconazole and saperconazole have greater water solubility than the diasteromeric mixtures of said compounds, in particular when complexed with cyclodextrin or its derivatives. As a result, pharmaceutical compositions having good bioavailability, yet comprising less cyclodextrin as a complexing agent, can be prepared.

The present invention is concerned with the stereoisomeric forms of itraconazole (X=Cl) and saperconazole (X=F), which may be represented by the formula cis-(I)

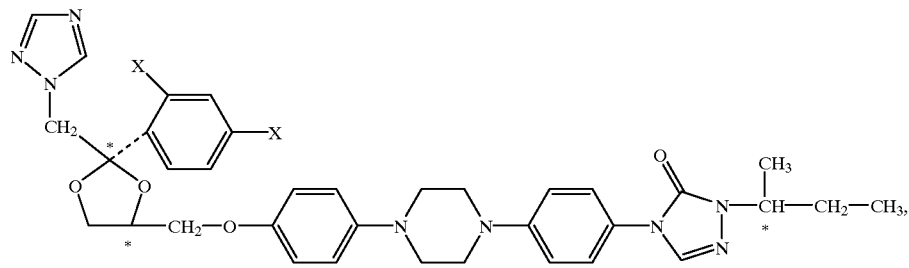

and the pharmaceutically acceptable acid addition salt forms thereof. The three asterisks indicate the three chiral centers, and 'cis' means that the (1H-1,2,4-triazol-1-ylmethyl) moiety and the substituted phenoxy moiety are located at the same side of the plane defined by the 1,3-dioxolane ring.

The four possible stereoisomeric cis forms can be described using various rules of nomenclature. The following tables show the correlation among the C.A. stereochemical descriptor, the absolute configuration at each of the chiral centers and the specific optical rotation $[\alpha]_D^{20}$ in 1% methanol (itraconazole; table I) (saperconazole; table II).

TABLE I

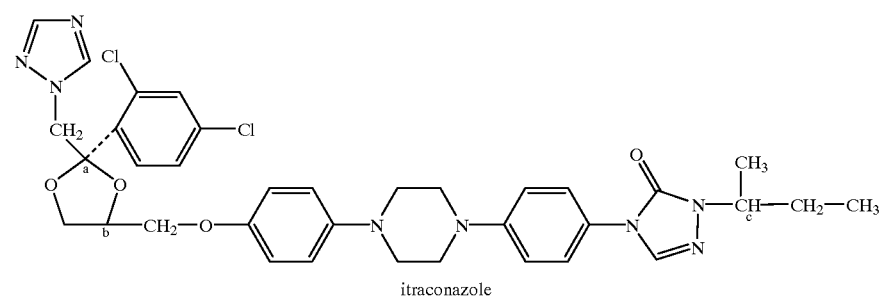

itraconazole

| C.A. descriptor | absolute configuration at | | | $[\alpha]_D^{20}$ |
|---|---|---|---|---|
| | (a) | (b) | (c) | (1% CH$_3$OH) |
| (+)-[2R-[2α,4α,4(R)]] | R | S | R | +14.15° |
| (+)-[2R-[2α,4α,4(S)]] | R | S | S | +19.08° |
| (−)-[2S-[2α,4α,4(R)]] | S | R | R | −18.78° |
| (−)-[2S-[2α,4α,r(S)]] | S | R | S | −13.46° |

TABLE II

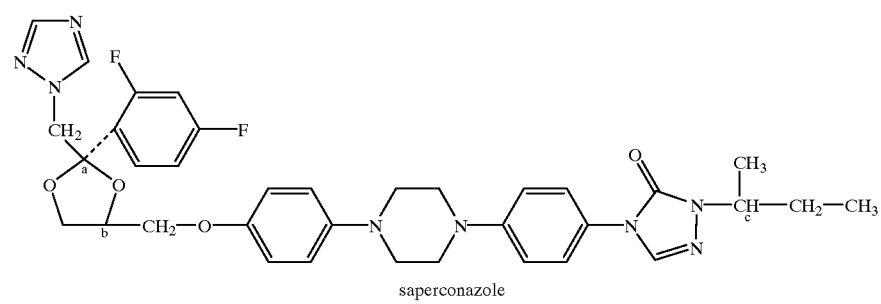

saperconazole

| C.A. descriptor | absolute configuration at | | | $[\alpha]_D^{20}$ |
|---|---|---|---|---|
| | (a) | (b) | (c) | (1% CH$_3$OH) |
| (+)-[2R-[2α,4α,4(R)]] | R | S | R | +9.00° |
| (+)-[2R-[2α,4α,4(S)]] | R | S | S | +14.13° |
| (−)-[2S-[2α,4α,4(R)]] | S | R | R | −13.55° |
| (−)-[2S-[2α,4α,4(S)]] | S | R | S | −8.41° |

The term 'stereoisomeric form' as used herein concerns compounds having a stereoisomeric purity of at least 96% up to a stereoisomeric purity of 100%, in particular compounds having a stereoisomeric purity of at least 98% up to 100%. In particular, said stereoisomeric forms define compounds having an enantiomeric excess and a diasteromeric excess of at least 96% up to 100%, more particularly, having an enantiomeric excess and a diastereoisomeric excess of 98% up to 100%.

With regard to the intermediates described hereinafter, the term "enantiomerically pure" defines intermediates having an enantiomeric excess of at least 96% up to 100%, more particularly, having an enantiomeric excess of 98% up to 100%.

The stereoisomeric forms of the compounds of formula (I) have basic properties. The pharmaceutically acceptable acid addition salts as mentioned hereinabove comprise the therapeutically active non-toxic acid addition salt forms which the compounds of formula (I) are able to form. Said salt forms can conveniently be obtained by treating the base form of the compounds of formula (I) with appropriate acids such as inorganic acids, for example, hydrohalic acid, e.g. hydrochloric, hydrobomic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydrxybutanedioic, 2-hydroxy-1,2,3-propanetricarboxylic, methanesulfonic, ethanesufonic, benzenesulfonic, 4-methylbenzenesulfonic, cyclohexanesulfamic, 2-hydroxybenzoic, 4-amino-2-hydroxybenzoic and the like acids. Conversely, the salt form can be converted by treatment with alkali into the free base form. The term acid addition salt also comprises the hydrates and solvent addition forms which the compounds of formula (I) are able to form. Examples of such forms are e.g. hydrates, alcholates and the like.

The four individual stereoisomeric forms of the compounds of formula (I) can be prepared by O-alkylating an enantiomerically pure phenol of formula (−)-(R)-(II) or (+)-(S)-(II) with an enantiomerically pure 1,3-dioxolane derivative of formula (−)-(2S,cis)-(III) or (+)-(2R,cis)-(III) wherein —OR represents a sulfonyloxy leaving group such as 4-methylbenzenesulfonyloxy (tosylate) or methanesulfonyloxy (mesylate).

The enantiomerically pure phenol of formula (−)-(R)-(II) can conveniently be prepared starting from (S)-2-butanol (IV). The enantiomeric (S)-butanol (IV) can be converted into a corresponding (S)-sulfonate (V) by reaction with 4-methylbenzenesulfonyloxy chloride (R=Me) or 1-bromo-4-benzenesulfonyl chloride (R=Br) in pyridine.

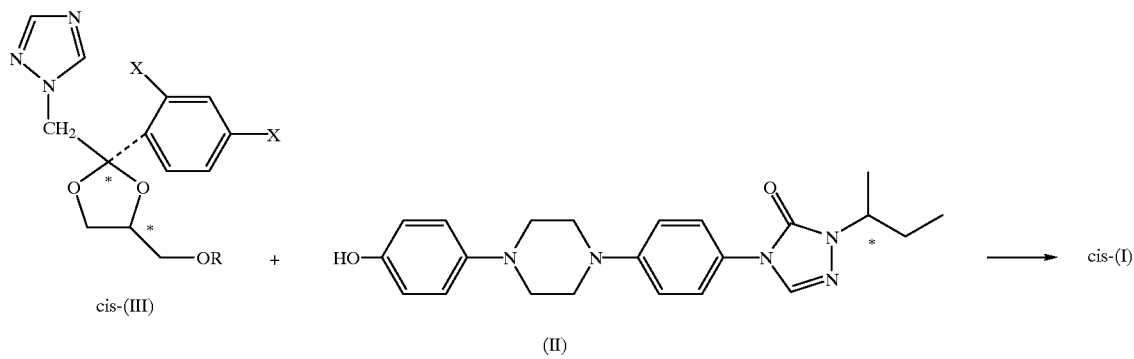

Said O-alkylation reaction can conveniently be conducted following art-known procedures, e.g. by stirring and heating the reactants in an appropriate solvent such as a dipolar aprotic solvent, e.g. N,N-dimethylformamide, N,N-dimethylacetamide and the like, in the presence of a base such as, an alkali metal hyroxide, e.g. sodium or potassium hydroxide. The thus obtained stereoisomeric forms of the compound of formula cis-(I) may be purified further following art-known methodologies such as liquid chromatography and crystallization.

The relation between the stereochemistry of the stereoisomeric forms of the compound of formula (I) obtained in said O-alkylation reaction and the stereochemistry of the starting materials (II) and (III) is shown in the table herebelow.

| cis-(I) | cis-(III) | (II) |
|---|---|---|
| (+)-[2R-[2a,4a,4(R)]] | (+)-(2R,cis)-(III) | (−)-(R)-(II) |
| (+)-[2R-[2a,4a,4(S)]] | (+)-(2R,cis)-(III) | (+)-(S)-(II) |
| (−)-[2S-[2a,4a,4(R)]] | (−)-(2S,cis)-(III) | (−)-(R)-(II) |
| (−)-[2S-[2a,4a,4(S)]] | (−)-(2S,cis)-(III) | (+)-(S)-(II) |

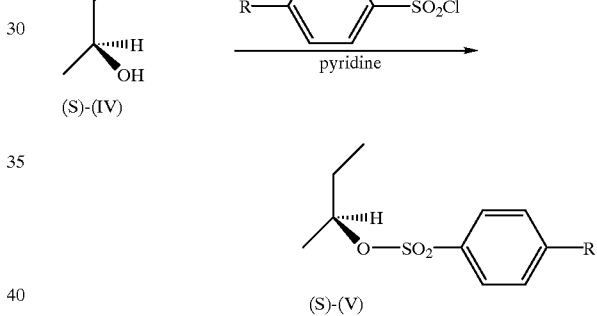

Enantioselective coupling of the sulfonate (S)-(V) with the triazolone (VI) (prepared as described in Example XVII of U.S. Pat. No. 4,267,179) proceeds with inversion of configuration at the chiral center and yields (−)-(R)-(VII).

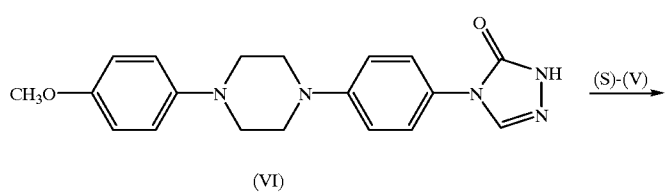

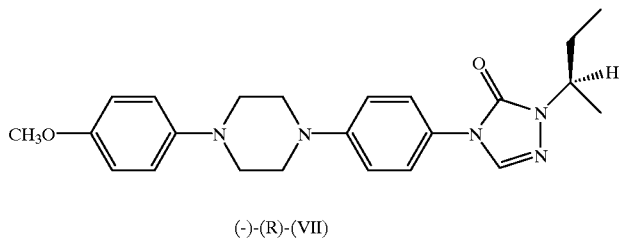

(-)-(R)-(VII)

Said coupling reaction can be conducted in a reaction inert solvent such as a dipolar aprotic solvent, preferably N,N-dimethylformamide, in the presence of a base such as sodium hydride. The enantiomeric excess of the thus obtained product (−)-(R)-(VII) ranges from about 65% to about 75% and can be increased up to an enantiomeric excess e.e. >98% by converting (−)-(R)-(VII) into the (R)-camphor sulfonate salt in acetone, followed by repeated recrystallization of the salt from ethanol/acetone mixtures (2:7; v/v).

Dealkylation of the thus purified anisole (−)-(R)-(VII) b heating to reflux in concentrated hydrobromic acid yields the enantiomerically pure phenol (−)-(R)-(II). In order to avoid bromination in the last mentioned step, it is advantageous to add sodium sulfite to the reaction mixture.

gained by using recycling peak shaving technology. For larger scale applications, the full continuous simulated moving bed adsorption technology can advantageously be used.

In an identical manner as described in the preceding paragraph, the racemate (±)-(II) can be separated into its two enantiomers on amylose tris-(3,5-dimethylphenyl) carbamate coated on a macroporous γ-aminopropyl silica matrix (Chiralpak AD™, Daicel).

The enantiomerically pure intermediate (+)-(2R,cis)(III) wherein —OR is tosylate, can be prepared from the commercially available (S)-2,2-dimethyl-1,3-dioxolane-4-yl methanol (S)-(VIII). Reaction of (S)-(VIII) with 4-methylbenzenesulfonyl chloride in pyridine and hydrolysis of the thus obtained product in an aqueous acid solution, e.g. hydrochloric acid 6N, optionally in admixture with

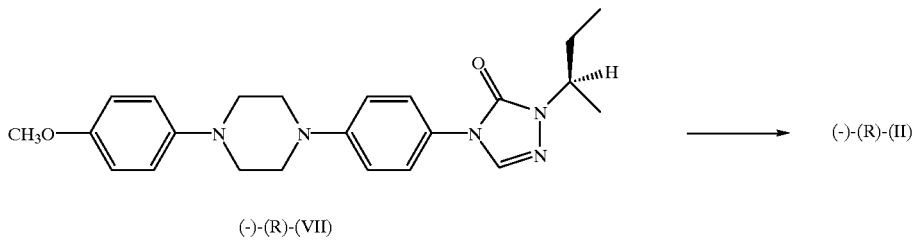

(-)-(R)-(VII) ⟶ (-)-(R)-(II)

The other enantiomeric form (+)-(S)-(II), can be prepared in a similar manner starting from (R)-2-butanol. Obviously, the optical purification of the thus obtained intermediate product (+)-(S)-(VII) is conducted on the (S)-camphor sulfonate salt.

An alternative procedure for preparing (−)-(R)-(VII) and (+)-(S)-(VII) comprises resolving the corresponding racemate (±)-(VII) by fractional crystallization with enantiomerically pure camphor sulfonic acid from a mixture of ethanol/acetone (1:4, v/v). Further optical purification to e.e. >98% can be achieved by repeatedly recrystallizing the camphor sulfonate salt as described hereinbefore. (−)-(R)-(VII) is obtained from recrystallizing the racemate (±)-(VII) with (R)-caphor sulfonic acid;
(R)-camphor sulfonic acid which are enriched in the (+)-(S)-(VII) enantiomer.

Preferably, however, the racemate (±)-(VII) can be resolved by liquid chromatography using a chiral stationary phase such as anylose derivative, in particular amylose tris-(3,5-dimethylphenyl) carbamate coated on a macroporous γ-aminopropyl silica matrix (Chiralpak AD™, Daicel), or a Pirkle type stationary phase. The separation is preferably conducted with an alcohol such as methanol or ethanol (optionally denatured with 1% methanol) as the mobile phase. In order to speed up the separation, the elution chromatography process may be conducted at a temperature higher than ambient (about 30° C.). More time can yet be solvent such as an alcohol or a ketone, e.g. acetone, yields the corresponding (R)-1,3-dihydroxypropyl tosylate (IX).

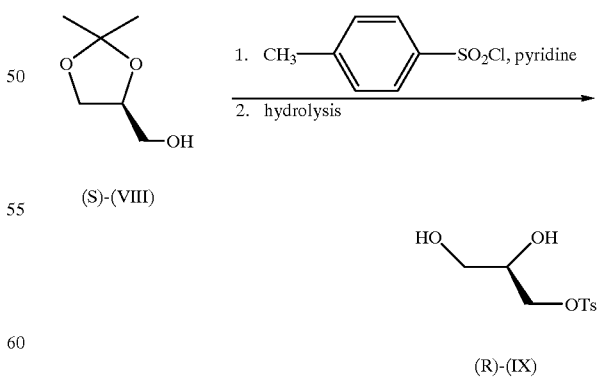

Acetalation of (R)-(IX) with 1-(2,4-dihalophenyl)-2-(1H-1,2,4-triazolyl)ethanone (X) under mild conditions yields a cis/trans mixture of dioxolanes from which the cis isomer (+)-(2R,cis)-(III) is obtained after chromatography.

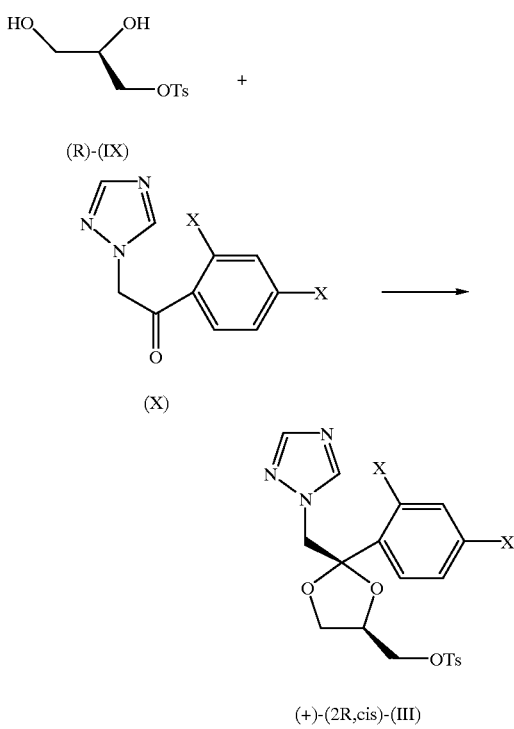

(R)-(IX)

(X)

(+)-(2R,cis)-(III)

Said acetalation reaction can conveniently be conducted by stirring and heating the reagents in a reaction-inert solvent, such as a halogenated hydrocarbon, e.g. dichloromethane or trichloromethane, in the presence of an acid, preferably a sulfonic acid, such as methanesulfonic acid.

In a similar manner, starting from (R)-2,2-dimethyl-1,3-dioxolane-4-yl methanol (R)-(VIII) there can be prepared (−)-(2S,cis)-(III).

The racemic compounds of formula (±)-cis(III)

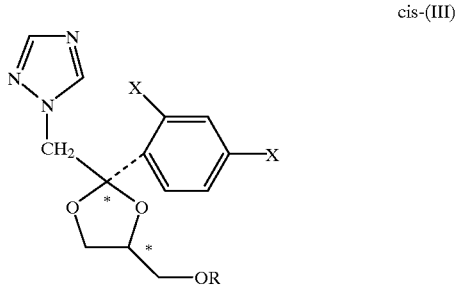

cis-(III)

wherein X represents chloro or fluoro and R represents 4-methylbenzenesulfonyl, methanesulfonyl, but also $C_{1-5}$alkylcarbonyl can conveniently be separated into their individual enantiomers by liquid chromatography using a chiral stationary phase such as a cellulose or amylose derived stationary phase. A preferred example of such a phase is cellulose tris-(4-methylbenzoate) either in its pure polymeric form or coated on a macroporous γ-aminopropyl silica matrix (Chiralcel OD™, Daicel). The mobile phase preferably is an alcohol such as methanol or ethanol (optionally denatured with 1% methanol). Methanol is preferred with the cellulose derivative in the pure polymeric form. In order to speed up the separation, the elution chromatography process may be conducted at a temperature higher than ambient (about 30° C.). More time can yet be gained by applying recycling peak shaving technology. For larger scale operations, the elution chromatography process is preferably replaced by full continuous simulated moving bed adsorption technology.

In case R represents $C_{1-5}$alkylcarbonyl, the separated enantiomers are converted into the mesylate or tosylate derivatives following art-known procedures such as saponifcation and subsequently sulfonylation.

The individual stereoisomeric forms of itraconazole and saperconazole have antifungal properties. Each of the four isomers contributes to the overall activity of the parent compound and none appears to be more active than said parent compound. The (−)-[2S-[2α,4α4(R)]] and (−)-[2S-[2α,4α,4(S)]] isomers however appear more potent than their respective enantiomorphs.

The individual stereoisomers of itraconazole and saperconazole can also be obtained by separating the diastereomeric mixture by liquid chromatography on a chiral stationary phase such as an amylose derivative, in particular amylose tris-(3,5-dimethylphenyl) carbamate coated on a macroporous γ-aminopropyl silica matrix (Chiralpak AD™, Daicel). Suitable mobile phases are alcohols in particular methanol and ethanol (optionally denatured with 1% methanol). In order to speed up the process and keep the product into solution, the separation is preferably performed at a temperature above ambient (up to 50° C.). Limitations to the separation process are the fact that the compounds are poorly soluble and only small amounts can be processed at one time. Furthermore, the occurrence of 4 peaks precludes the use of recycling and peak-shaving technology. Consequently, separation of the intermediates for preparing stereochemically pure itraconazole and saperconazole is to be preferred over the separation of the end-products.

The individual stereoisomeric forms of itraconazole and saperconazole have greater water solubility than the diasteromeric mixtures of said compounds particularly when the individual stereoisomers are complexed with a cyclodextrin derivative.

Appropriate cyclodextrin derivatives are α-, β-, γ-cyclodextrins or ethers and mixed ethers thereof wherein one or more of the hydroxy groups of the anhydroglucose units of the cyclodextrin are substituted with $C_{1-6}$alkyl, particularly methyl, ethyl or isopropyl; hydroxyl $C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkylcarbonyl, particularly acetyl; $C_{1-6}$alkyloxycarbonyl$C_{1-6}$alkyl or carboxy$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD.

The term mixed ether denotes cyclodextrin derivatives wherein at least two cyclodextrin hydroxy groups are etherified with different groups such as, for example, hydroxypropyl and hydroxyethyl.

The average molar substitution (M.S.) is used as a measure of the average number of moles of alkoxy units per mole of anhydroglucose. In the cyclodextrin derivatives for use in the compositions according to the present invention the M.S. is in the range of 0.125 to 10, in particular of 0.3 to 3, or from 0.3 to 1.5. Preferably the M.S. ranges from about 0.3 to about 0.8, in particular from about 0.35 to about 0.5 and most particular is about 0.4.

The average substitution degree (D.S.) refers to the average number of substituted hydroxyls per anhydroglucose unit. In the cyclodextrin derivatives for use in the compositions according to the present invention the D.S. is in the range of 0.125 to 3, in particular of 0.2 to 2 or from 0.2 to 1.5. Preferably the D.S. ranges from about 0.2 to about 0.7, in particular from about 0.35 to about 0.5 and most particularly is about 0.4.

More particular β- and γ-cyclodextrin hydroxyalkyl derivatives for use in the compositions according to the present invention are partially substituted cyclodextrin derivatives wherein the average degree of alkylation at hydroxyl groups of different positions of the anhydroglucose units is about 0% to 20% for the 3 position, 2% to 70% for the 2 position and about 5% to 90% for the 6 position. Preferably the amount of unsubstituted β- or γ-cyclodextrin less than 5% of the total cyclodextrin content and in particular is less than 1.5%. Another particularly interesting cyclodextrin derivative is randomly methylated β-cyclodextrin.

Most preferred cyclodextrin derivatives for use in the present invention are those partially substituted β-cyclodextrin ethers or mixed ethers having hydroxypropyl, hydroxyethyl and in particular 2-hydroxypropyl and/or 2-(1-hydroxypropyl) substituents.

The most preferred cyclodextrin derivative for use in the compositions of the present invention is bydroxypropyl-β-cyclodextrin having a M.S. in the range of from 0.35 to 0.50 and containing less than 1.5% unsubstituted β-cyclodextrin.

Substituted cyclodextrins can be prepared according to procedures described in U.S. Pat. No. 3,459,731, EP-A-0, 149,197, EP-A-0,197,571, U.S. Pat. No. 4,535,152, WO-90/12035 and GB-2,189,245.

Other references describing cyclodextrins for use in the compositions according to the present invention, and which provide a guide for the preparation, purification and analysis of cyclodextrins include the following: "Cyclodextrin Technology" by József Szejtli, Kluwer Academic Publishers (1988) in the chapter Cyclodextrins in Pharmaceuticals; "Cyclodextrin Chemistry" by M. I. Bender et al., Springer-Verlag, Berlin (1978); "Advances in Carbohydrate Chemistry", Vol. 12 Ed. by M. I. Wolfrom, Academic Press, New York (157) in the chapter The Schaardinger Dextrins by Dexter French at p. 189–260; "Cyclodextrins and their Inclusions Complexes" by J. Szejtli, Akademiai Kiado, Budapest, Hungary (1982); I. Tabushi in Acc. Chem. Research, 1982, 15, p. 66–72; W. Sanger, Angewandte Chemie, 92, p. 343–361 (1981); A. P. Croft and R. A. Bartsch in Tetrahedron, 39, p. 1417–1474 (1983); Irie et al. Pharmaceutical Research, 5, p. 713–716, (1988); Pitha et al. Int. J. Pharm. 29, 73, (1986); DE 3118218; DE 3,317,064; EP-A-94,157; U.S. Pat. No. 4,659,696; and U.S. Pat. No. 4,383,992. Particular attention should be paid to those references which describe the preparation and purification methods which provide cyclodextrin mixtures wherein the amount of unreacted cyclodextrin is less than 5% of the total cyclodextrin content.

The complexes of the individual stereoisomeric compounds of formula (I) with cyclodextrin derivatives as mentioned hereinabove, can conveniently be prepared by dissolving the cyclodextrin or ether derivative thereof in water and adding thereto the individual stereoisomeric compound of formula (I) while stirring or shaking the resulting mixture until complete dissolution is obtained. For storage purposes it may be advantageous to dehydrate the thus obtained solutions, e.g. by freeze-drying or spray-drying. The dehydrated complexes can easily be reconstituted by the addition of water or an aqueous cyclodextrin solution.

The complexes of the individual stereoisomeric compounds of formula (I) with cyclodextrin derivatives are particularly useful for the preparation of pharmaceutical compositions for oral, parenteral or topical administration. Said pharmaceutical compositions comprise as active ingredient a complex as defined hereinabove and a pharmaceutically acceptable carrier. Said carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable deleterious effect nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In the final compositions, the cyclodextrin will comprise about 2.5 to 20% by weight, in particular about 5 to 20%, more in particular 5 to 15%, for example about 10%, with the remainder being water, the active ingredient and any excipients.

In particular, stable pharmaceutical compositions may consist of water, cyclodextrin and the active ingredient alone without the need of additional stabilizers such as, human serum albumin, bovine serum albumin, lecithin, methyl cellulose, polyethylene glycol, sulfur containing reducing agents, urea, amino acids and surfactants. There may be added a pH-adjusting agent e.g. hydrochloric acid, acetic acid, citric acid, sodium hydroxide, potassium hydroxide or a salt of any of these, in particular sodium citrate. The appropriate pH for formulating the itraconazole or saperconazole stereoisomers ranges from 6.5 to 7.4, in particular from 6.8 to 7.0. Appropriate preservatives for the above pharmaceutical preparations are: alcohols, for example, ethanol, 1,3-propanediol, benzylalcohol or derivatives thereof, phenyl ethyl alcohol, phenol or phenol derivatives such as butylparaben, methylparaben, m-cresol or chlorocresol; acids, for example, benzoic acid, sorbic acid, citric acid, sodium propionate, EDTA disodium; chlorhexidine; hexamidine diisetionate; hexetidine; optionally in combination with sodium bisulfite, or with propyleneglycol, or less preferably quaternary ammonium salts, metallic compounds such as zinc oxide, thiomersal and phenyl mercury salts, e.g. phenylmercuric acetate.

For the preparation of an injectable it is appropriate to add an isotonizing agent, e.g. sodium chloride, potassium chloride, sorbitol.

It may further be appropriate to add a suitable complexing agent such as calcium chloride, citrate, EDTA and the like pharmaceutically acceptable metal ion complexing agents. For example, there may be added calcium chloride at a concentration of about 0.02–2 g/l.

Said compositions can conveniently be prepared by dissolving the cyclodextrin or ether derivative thereof in water and adding thereto the compound of formula (I) as well as other adjuvants and components such as, for example, sodium chloride, potassium nitrate, glucose, mannitol, sorbitol, xylitol and buffers such as, for example, phosphate, acetate or citrate buffer; and optionally concentrating or drying the solution by evaporation under reduced pressure or by lyophilization; and further optionally reconstituting the lyophilized residue with water.

Preferred preparations according to the present invention have low toxicity, and are not irritating, thus permitting the manufacture of an injectable medicament which may safely be used in repeated dose regimes without the risk of immunogenic reactions.

The aqueous preparations according to invention, and an excipient if required, may also be freeze-dried or spray-dried following art-known procedures to give a dehydrated composition which may be stored for a long period of time and dissolved before administration. In said freeze-dried or spray-dried formulations the molar ratio and the weight-to-weight ratio of cyclodextrin to active ingredient may be the same as in the above-mentioned aqueous solutions. As it is convenient in a number of instances to reconstitute said freeze-dried or spray-dried formulation in an aqueous cyclodextrin solution, the molar ratio and the weight to weight ratio of cyclodextrin to active ingredient may also be lower than in the above mentioned aqueous solutions.

EXPERIMENTAL PART

A. Preparation of the intermediates

EXAMPLE 1

To a solution of 40.5 g of 1-(2,4-dichlorophenyl)-2-(1H-1,2,4-triazol-1-yl) ethanone in 300 ml of methanesulfonic acid and 300 ml of dichloromethane, were added dropwise 41.4 g of (S)-1,2,3-propanetriol 4-methylbenzenesulfonate (ester). The reaction mixture was stirred for 4 days at reflux temperature using a water separator. After cooling, the whole was added dropwise (over 1 hour) to a mixture of $K_2CO_3$ (3.6 M), 500 g of ice and 500 ml of trichloromethane while stirring. Stirring was continued for 1 hour and then the organic layer was separated. The aqueous layer was extracted with trichloromethane (3×) and the combined extracts were washed with water (2×) and evaporated. The residue was purified by column chromatography (silica gel; $CHCl_3$). The eluent of the desired fraction was evaporated and the residue was converted into the 4-methylbenzenesulfonate salt (1:1) in 4-methyl-2-pentanone. The salt was filtered off and dried, yielding 27.0 g (26.9%) of (−)-(2S,cis)-2-(2,4-dichlorophenyl)-2-(1H-1,2,4-triazol-1-ylmethyl)-1,3-dioxolane-4-methanol. 4-methylbenzenesulfonate (ester) 4-methylbenzenesulfonate (1:1salt); mp. 194.5° C.; $[\alpha]_D^{20}=-16.37°$ (c=1% in methanol) (interm. 1).

EXAMPLE 2

To a stirred solution of 12.8 g of 1-(2,4-dichlorophenyl)-2-(1H-1,2,4-triazol-1-yl) ethanone in 72.2 ml of dichloromethane were added dropwise 15 ml of methanesulfonic acid during 15 minutes at room temperature. Upon complete addition, 14.8 g of (2R)-1,2,3-propanetriol 4-methylbenzenesulfonate (ester) were added and the whole was stirred and refluxed for 48 hours with the azetropical removal of water. The previous mixture was added dropwise to a mixture of 195.5 ml of dichloromethane and a solution of 50 g of potassium carbonate in 200 ml of water, After stirring for a while, the separated organic layer was dried, filtered and evaporated. The residue was purified by column chromatography over silica gel using trichloromethane as eluent. The pure fractions were collected and the eluent was evaporated. The residue was converted into the 4-methylbenzenesulfonate salt in 4-methyl-2-pentanone. The product was filtered off and dried, yielding 6.1 g (18.5%) of (+)-(2R,cis)-2-(2,4-dichlorophenyl)-2-(1H-1,2,4-triazol-1-ylmethyl)-1,3-dioxolane-4-methanol. 4-methylbenzenesulfonate (ester) 4-methylbenzenesulfonate (1:1salt); mp. 194.0° C.; $[\alpha]_D^{20}=+16.44°$ (conc.=1% in ethanol) (interm. 2).

EXAMPLE 3 a) A mixture of 8.2 g of (R)-(−)2-butanol, 31.5 g of 1-bromo-4-benzenesulfonyl chloride, 1.0 g of N,N-dimethyl-4-pyridinamine, 55.5 ml of pyridine and 293 ml of dichloromethane was stirred for 3 days at room temperature. After the addition of water, stirring was continued for 1 hour. The reaction mixture was washed twice with a diluted hydrochloric acid solution and once with water, dried, filtered and evaporated in vacuo. The residue was purified by column chromatography over silica gel using trichloromethane as eluent. The pure fractions were collected and the eluent was evaporated, yielding 11.5 g (35.6%) of (R)-2-butanol 4-bromobenzenesulfonate (ester) (interm. 3).

In a similar manner, (S)-(+)-2-butanol and 4-methylbenzenesulfonyl chloride were converted into (S)-2-butanol 4-methylbenzenesulfonate (ester) (interim 4).

b) A mixture of 3.5 g of (2,4-dihydro-4-[4-[4-(4-methoxyphenyl)-1-piperazinyl]-phenyl]-3H-1,2,4-triazol-3-one, 0.6 g of a sodium hydride dispersion 50% and 100 ml of N,N-dimethylformamide was stirred for 3 hours at 80° C. After the addition of 3.5 g of (R)-2-butanol 4-bromobenzenesulfonate (ester) (intermediate (3)), stirring was continued for 6 hours at this temperature. After cooling, waster was added. The crystallized product was filtered off and taken up in trichloromethane. The undissolved part was filtered off. The remaining solution was dried and purified by column chromatography over silica gel using trichloromethane as eluent. The pure fractions were collected and the eluent was evaporated. The residue was crystallized from 4-methyl-2-pentanone. The product was filtered off and converted into the (S)-7,7-dimethyl-2-oxobicyclo[2.2.1]

heptane-1-methanesulfonate salt in 2-propanone. The salt was filtered off and recrystallized from 1-butanol. The product was filtered off and dried, yielding 1.2 g (13.7%) of (+)-(S)-2,4-dihydro-4-[4-[4-(4-methoxyphenyl)-1-piperazinyl]-phenyl]-2-(1-methylpropyl)-3H-1,2,4-triazol-3-one (S)-7,7-dimethyl-2-oxobicyclo[2.2.1]heptane-1-methanesulfonate (1:2); mp. 192.0° C.; $[\alpha]_D^{20}$=+28.41° (conc.=1% in ethanol) (interm. 5).

In a similar manner, intermediate 4 was converted into (−)-(R)-(2,4-dihydro-4-[4-[4-(4-methoxyphenyl)-1-piperazinyl]-phenyl]-2-(1-methylpropyl)-3H-1,2,4-triazol-3-one, (R)-7,7-dimethyl-2-oxobicyclo[2.2.1]heptane-1-methanesulfonate (1:2); mp. 193.0° C.; $[\alpha]_D^{20}$=−28.02° (conc.=1% in ethanol) (interm. 6).

c) A mixture of 29.4 g of (+)-(S)-(2,4-dihydro-4-[4-[4-(4-methoxyphenyl)-1-piperazinyl]-phenyl]-2-(1-methylpropyl)-3H-1,2,4-triazol-3-one, (S)-7,7-dimethyl-2-oxobicyclo[2.2.1]heptane-1-methanesulfonate (1:2) (intermediate (5)), 2.0 g of sodium sulfite and 151 ml of a hydrobromic acid solution 48% in water was stirred for 5 hours at reflux temperature. The reaction mixture was cooled to room temperature and water was added. The while was neutralized with potassium carbonate to pH 7 while stirring in a mixture of dichloromethane and 1-butanol (90:10 by volume). The separated organic layer was dried, filtered and evaporated in vacuo. The residue was triturated in methanol. The precipitated product was filtered off and purified by column chromatography over silica gel using a mixture of trichloromethane and methanol (98:2 by volume) as eluent. The pure fractions were collected and the eluent was evaporated. The residue was crystallized from 4-methyl-2-pentanone. The product was filtered off and dried, yielding 10.4 g (77.7%) of (+)-(S)-(2,4-dihydro-4-[4-[4-(4-hydroxyphenyl)-1-piperazinyl]-phenyl]-2-(1-methylpropyl)-3H-1,2,4-triazol-3-one; mp. 180.6° C.: $[\alpha]_D^{20}$=+4.38° (conc.=1% in methanol) (interm. 7).

In a similar manner, intermediate 6 was converted into (−)-(R)-(2,4-dihydro-4-[4-[4-(4-hydroxyphenyl)-1-piperazinyl]-phenyl]-2-(1-methylpropyl)-3H-1,2,4-triazol-3-one; mp. 180.4° C.: $[\alpha]_D^{20}$=+4.16° (conc.=1% in methanol) (interm. 8).

EXAMPLE 4

A mixture of 44.6 g of 1-(2,4-difluorophenyl)-2-(1H-1,2,4-triazol-1-yl)ethanone, 56.0 g of (2S)-1,2,3-propanetriol 4-methylbenzenesulfonate (ester), 200 ml of methanesulfonic acid and 150 ml of dichloromethane was stirred at reflux temperature using a water separator. After cooling, the reaction mixture was added dropwise to a mixture of ice-water, $K_2CO_3$ (aq.) and dichloromethane. The organic layer was separated and the aqueous phase was re-extracted with dichloromethane. The combined dichloromethane layers were dried, filtered and evaporated. The residue was purified by column chromatography (silica gel: $CHCl_3$). The eluent of the desired fraction was evaporated and the residue was converted into the 4-methylbenzenesulfonate salt in 4-methyl-2-pentanone. The salt was recrystallized from 4-methyl-2-pentanone, yielding 20.5 g (16.4%) of (−)-(2S, cis)-2-(2,4-difluorophenyl)-2-(1H-1,2,4-triazol-1-ylmethyl)-1,3-dioxolane-4-methanol 4-methylbenzenesulfonate (ester) 4-methylbenzenesulfonate (salt 1:1); mp. 182.5° C.; $[\alpha]_D^{20}$=−13.79° C. (c=1% in $CH_3OH$) (interim 9).

EXAMPLE 5

A mixture of 40.0 g of 1-(2,4-difluorophenyl)-2-(1H-1,2,4-triazol-1-yl)ethanone, 56.0 g of (2R)-1,2,3-propanetriol 1-(4-methylbenzenesulfonate) (ester), 250 ml of methanesulfonic acid and 100 ml of dichloromethane was stirred for 24 hours at reflux temperature using a water separator. After cooling, the reaction mixture was added dropwise to a mixture of $K_2CO_3$, water, ice and dichloromethane. The dichloromethane layer was separated, washed with water, dried, filtered and evaporated. The residue was purified by column chromatography (silica gel: $CHCl_3$). The eluent of the desired fraction was evaporated and the residue was converted into the 4-methylbenzenesulfonate salt in 4-methyl-2-pentanone. The salt was recrystallized from acetonitrile, yielding 23.1 g (20.6%) of (+)-(2R,cis)-2-(2,4-difluorophenyl)-2-(1H-1,2,4-triazol-1-ylmethyl)-1,3-dioxolane-4-methanol 4-methylbenzenesulfonate(ester) 4-methylbenzenesulfonate (salt 1:1); mp. 183.5° C.; $[\alpha]_D^{20}$=+14.43 (conc.=1% in methanol) (interm. 10).

EXAMPLE 6

A solution of 4 g of 2,4-dihydro-4-[4-[4-(4-hydroxyphenyl)-1-piperazinyl]phenyl]-2-(1-methylpropyl)-3H-1,2,4-triazol-3-one in 600 ml of methanol was resolved by liquid chromatography. Details of the chromatography process were:

column: 400 mm×100 mm I.D. filled with about 1 Kg. 20 μm amylose tris-(3,5-dimethylphenyl) carbamate (Chiralpak AD™; Daicel)

mobile phase: 150 ml/min. ethanol temperature: 30° C.

The 4 g sample was separated in three cycles and yielded two fractions comprising 95–97% of the theoretical yield (mp. 158–162° C.). Optical purity as determined by High Performance Liquid Chromatography was 97% (interm. 11 and 12).

EXAMPLE 7

A solution of 5 g (±)-cis-2-(2,4-difluorophenyl)-2-(1H-1,2,4-triazol-1-ylmethyl)-1,3-dioxolane-4-methanol 4-methylbenzenesulfonate (ester) in 500 ml of methanol was resolved by liquid chromatography. Details of the chromatography process were: column: 500 mm×100 mm I.D. filled with about 2 Kg. 20 μm cellulose tris-(4-methyl benzoate) (Chiralcel OJ™: Daicel)

mobile phase: 150 ml/min. ethanol temperature: 30° C.

The 5 g sample was separated in three cycles and yielded (−) compound (93–95% yield, HPLC purity: 100%; α (365 mm)'−34.69° (1% MeOH); mp 92–94° C.) (interm. 13) and (+) compound (95–96% yield, HPLC purity: 98.8% α (365 mm)=+34.02° (1% MeOH); mp 92–94° C.) (interm. 14).

B. Preparation of the final compounds

EXAMPLE 8

A mixture of 5.2 g of (+)-(2R,cis)-2-(2,4-dichlorophenyl)-2-(1H-1,2,4-triazol-1-ylmethyl)-1,3-dioxolane-4-methanol 4-methylbenzenesulfonate (ester) 4-methylbenzenesulfonate (salt 1:1) (intermediate (2)), 2.9 g of (+)-(S)-2,4-dihydro-4-[4-[4-[(4-hydroxyphenyl)-1-piperazinyl]phenyl]-2-(1-methylpropyl)-3H-1,2,4-triazol-3-one (intermediate (7)), 1.0 g of sodium hydroxide flakes and 100 ml of N,N-dimethylformamide was stirred for 7 hours at 50° C. under a nitrogen atmosphere. After cooling, water was added to the reaction mixture. The precipitate was filtered off and taken up in trichloromethane. The organic layer was washed with water, dried, filtered and evaporated.

The residue was purified by column chromatography (silica gel; CHCl₃/CH₃OH 98.5:1.5). The eluent of the desired fraction was evaporated and the residue was triturated in methanol, yielding 3.9 g (79.0%) of (+)-[2R-[2α,4α,4(S)]]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one; mp. 175.3° C.; $[\alpha]_D^{20}$=+19.08° (c=1% in methanol) (comp. 1).

EXAMPLE 9

A mixture of 6.5 g of (−)-(2S,cis)-2-(2,4-dichlorophenyl)-2-(1H-1,2,4-triazol-1-ylmethyl)-1,3-dioxolane-4-methanol 4-methylbenzenesulfonate (ester) 4-methylbenzenesulfonate (salt 1:1) (intermediate (1)), 3.6 g of (+)-(S)-2,4-dihydro-4-[4-[4-[(4-hydroxyphenyl)-1-piperazinyl]phenyl]-2-(1-methylpropyl)-3H-1,2,4-triazol-3-one (intermediate (7)), 1.0 g of sodium hydroxide flakes and 100 ml of N,N-dimethylformamide was stirred overnight at 50° C. under a nitrogen atmosphere. After cooling, water was added to the reaction mixture. The precipitate was filtered off, washed with water and taken up in dichloromethane. The organic layer was washed with water, dried, filtered and evaporated. The residue was triturated in methanol, yielding 4.6 g (72.5%) of (−)-[2S-[2α,4α,4(S)]]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one; mp. 146.5° C.; $[\alpha]_D^{20}$=−13.46° (c=1% in methanol) (comp. 2).

EXAMPLE 10

A mixture of 6.5 g of (−)-(2S,cis)-2-(2,4-dichlorophenyl)-2-(1H-1,2,4-triazol-1-ylmethyl)-1,3-dioxolane-4-methanol 4-methylbenzenesulfonate (ester) 4-methylbenzenesulfonate (salt 1:1) (intermediate (1)), 3.6 g of (−)-(R)-2,4-dihydro-4-[4-[4-[(4-hydroxyphenyl)-1-piperazinyl]phenyl]-2-(1-methylpropyl)-3H-1,2,4-triazol-3-one (intermediate (8)), 1.0 g of sodium hydroxide flakes and 100 ml of N,N-dimethylformamide was stirred overnight at 50° C. under a nitrogen atmosphere. After cooling, water was added to the reaction mixture. The precipitate was filtered off, washed with water and taken up in dichloromethane. The organic layer was washed with water, dried, filtered and evaporated. The residue was triturated in methanol, yielding 4.4 g (69.3%) of (−)-[2S-[2α,4α,4(R)]]-4-[4-[4-[4-[[2-(2,4-dichlorophenyl)-2-(1H-1,2,4-triazol-1-ylmethyl)-1,3-dioxolan-4-yl]methoxy]phenol]-1-piperazinyl]phenyl]-2,4-dihydro-2-(1-methylpropyl)-3H-1,2,4-triazol-3-one; mp. 156.6° C.; $[\alpha]_D^{20}$=+13.46° (c=1% in methanol) (comp. 3).

EXAMPLE 11

A mixture of 6.5 g of (+)-(2R,cis)-2-(2,4-dichlorophenyl)-2-(1H-1,2,4-triazol-1-ylmethyl)-1,3-dioxolane-4-methanol 4-methylbenzenesulfonate (ester) 4-methylbenzenesulfonate (salt 1:1) (intermediate (2)), 3.6 g of (+)-(S)-2,4-dihydro-4-[4-[4-[(4-hydroxyphenyl)-1-piperazinyl]phenyl]-2-(1-methylpropyl)-3H-1,2,4-triazol-3-one (intermediate (8)), 1.0 g of sodium hydroxide flakes and 100 ml of N,N-dimethylformamide was stirred overnight at 50° C. under a nitrogen atmosphere. After cooling, water was added to the reaction mixture. The precipitate was filtered off, washed with water and taken up in trichloromethane. The organic layer was dried, filtered and evaporated. The residue was triturated in methanol. The product was dried in vacuo at 100° C., yielding 4.7 g (74%) of (+)-[2R-[2α,4α,4(R)]]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one; mp. 148.0° C.; $[\alpha]_D^{20}$=+14.15° (c=1% in methanol) (comp. 4).

EXAMPLE 12

A mixture of 11.7 g of (−)-(2S,cis)-2-(2,4-dichlorophenyl)-2-(1H-1,2,4-triazol-1-ylmethyl)-1,3-dioxolane-4-methanol 4-methylbenzenesulfonate (ester) 4-methylbenzenesulfonate (salt 1:1) (intermediate (9)), 6.6 g of (+)-(S)-2,4-dihydro-4-[4-[4-[(4-hydroxyphenyl)-1-piperazinyl]phenyl]-2-(1-methylpropyl)-3H-1,2,4-triazol-3-one (intermediate (7)), 1.5 g of sodium hydroxide flakes and 150 ml of N,N-dimethylformamide was stirred overnight at 50° C. under a nitrogen atmosphere. After cooling, water was added to the reaction mixture. The precipitate was filtered off, washed with water and taken up in dichloromethane. The organic layer was dried, filtered and evaporated. The residue was triturated in methanol, yielding 10.1 g (88.3%) of (−)-[2S-[2α,4α,4(S)]]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one; mp. 179.7° C.; $[\alpha]_D^{20}$=−8.41° (c=1% in methanol) (comp. 5).

EXAMPLE 13

A mixture of 9.3 g of (−)-(2S,cis)-2-(2,4-dichlorophenyl)-2-(1H-1,2,4-triazol-1-ylmethyl)-1,3-dioxolane-4-methanol 4-methylbenzenesulfonate (ester) 4-methylbenzenesulfonate (salt 1:1) (intermediate (9)), 5.5 g of (−)-(R)-2,4-dihydro-4-[4-[4-[(4-hydroxyphenyl)-1-piperazinyl]phenyl]-2-(1-methylpropyl)-3H-1,2,4-triazol-3-one (intermediate (8)), 1.0 g of sodium hydroxide flakes and 150 ml of N,N-dimethylformamide was stirred overnight at 50° C. under a nitrogen atmosphere. After cooling, 800 ml of water was added. The precipitate was filtered off and taken up in dichloromethane. The organic layer was washed with water, dried, filtered and evaporated. The residue was purified by column chromatography (silica gel; CHCl₃/CH₃OH 98.5:1.5). The eluent of the desired fraction was evaporated and the residue was triturated in methanol, yielding 7.7 g (81.8%) of (−)-[2S-[2α,4α,4(S)]]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one; mp. 183.3° C.; $[\alpha]_D^{20}$=−13.55° (c=1% in methanol) (comp. 6).

EXAMPLE 14

A mixture of 9.9 g of (+)-(2R,cis)-2-(2,4-dichlorophenyl)-2-(1H-1,2,4-triazol-1-ylmethyl)-1,3-dioxolane-4-methanol 4-methylbenzenesulfonate (ester) 4-methylbenzenesulfonate (salt 1:1) (intermediate (10)), 5.5 g of (−)-(R)-2,4-dihydro-4-[4-[4-[(4-hydroxyphenyl)-1-piperazinyl]phenyl]-2-(1-methylpropyl)-3H-1,2,4-triazol-3-one (intermediate (8)), 2.0 g of sodium hydroxide flakes and 150 ml of N,N-dimethylformamide was stirred overnight at 50° C. under a nitrogen atmosphere. After cooling, water was added to the reaction mixture. The precipitate was filtered off and taken up in dichloromethane. The organic layer was dried, filtered and evaporated. The residue was crystallized from methanol, yielding 8.3 g (88.1%) of (+)-[2R-[2α,4α,4(R)]]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1- methylpropyl)-3H-1,2,4-triazol-3-one; mp. 180.6° C.; $[\alpha]_D^{20}$=+9.00° (c=1% in methanol) (comp. 7).

EXAMPLE 15

A mixture of 6.7 g of (+)-(2R,cis)-2-(2,4-difluorophenyl)-2-(1H-1,2,4-triazol-1-ylmethyl)-1,3-dioxolane-4-methanol 4-methylbenzenesulfonate (ester) 4-methylbenzenesulfonate (salt 1:1) (intermediate (10)), 3.9 g of (+)-(S)-2,4-dihydro-4-[4-[4-[(4-hydroxyphenyl)-1-piperazinyl]phenyl]-2-(1-methylpropyl)-3H-1,2,4-triazol-3-one (intermediate (7)), 1.5 g of sodium hydroxide flakes and 100 ml of N,N-dimethylformamide was stirred overnight at 50° C. under a nitrogen atmosphere. After cooling, water was added to the reaction mixture. The precipitate was filtered off and taken up in dichloromethane. The organic layer was dried, filtered and evaporated. The residue was triturated with methanol, yielding 5.6 g (83.2%) of (+)-[2R-[2α,4α,4(S))]-4-[4-[4-[4-[[2-(2,4-difluorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one; mp. 182.4° C.; $[\alpha]_D^{20}$=+14.13° (c=1% in methanol) (comp. 8).

C. Physiochemical examples

EXAMPLE 16

The solubility of the individual stereoisomeric forms of itraconazole and saperconazole in water, either in the absence or in the presence of different concentrations of 2-hydroxypropyl-β- cyclodextrin and at ambient temperature, was determined by preparing saturated solutions and measuring the amount of dissolved active ingredient. A 10 ml stock solution comprising 0, 2.5, 5, 7.5, 10, 20, 30 or 40% (weight by volume) 2-hydroxypropyl-β-cyclodextrin (M.S.=0.4) was put in a 20 ml tinted vial. To each vial there was added a quantity of itraconazole or saperconazole sufficient to yield a saturated solution. The vials were sonicated for 10 minutes and all vials were checked to ascertain that an undissolved remnant remained. Where all the material had dissolved, another quantity of the material was added. The vials were closed and protected from light by wrapping them in aluminum foil. The vials were then shaken in an appropriate apparatus. 24 Hours later the vials were checked again to ascertain that an undissolved remnant of the material remained and where necessary a further quantity of the material was added. The vials were shaken for at least 72 hours and then allowed to stand until all undissolved material had precipitated. The vials were opened and the pH of the saturated solutions was measured. An aliquot of the supernatant solution was filtered and the amount of dissolved active ingredient was measured by UV spectrometry (255 nm), if necessary after diluting said aliquot to a concentration suitable for UV spectrometry.

The tables hereinbelow summarize the concentrations (mg/100 ml) of itraconazole and its individual stereoisomeric forms, and of saperconazole and its individual stereoisomeric forms, in water either in the absence or presence of different concentrations of 2-hydroxypropyl-β-cyclodextrin.

TABLE 1

| | | (itraconazole) | | | | | | | |
|---|---|---|---|---|---|---|---|---|---|
| active | | 2-hydroxypropyl-β-cyclodextrin concentration | | | | | | | |
| ingredient | stereochemistry | 0% | 2.5% | 5% | 7.5% | 10% | 20% | 30% | 40% |
| | cis (mixture of 4 isomers) itraconazole | n.d. | 0.36 | 1.79 | 4.74 | 10.28 | 50 | 95 | 174 |
| 1 | (+)-[2R-[2α, 4α, 4(S)]] | n.d. | 2.77 | 16.21 | 39.64 | 78.98 | 354 | 889 | 1783 |
| 2 | (−)-[2S-[2α, 4α, 4(S)]] | n.d. | 3.58 | 16.36 | 41.39 | 78.16 | 332 | 846 | 1720 |
| 3 | (−)-[2S-[2α, 4α, 4(R)]] | n.d. | 2.01 | 14.21 | 37.64 | 96.40 | 371 | 1045 | 1860 |
| 4 | (+)-[2R-[2α, 4α, 4(R)]] | n.d. | 2.43 | 15.84 | 41.70 | 83.72 | 481 | 1166 | 2017 | n.d.: not detectable by U.V. spectrometry

TABLE 2

| | | (saperconazole) | | | | |
|---|---|---|---|---|---|---|
| active | | 2-hydroxypropyl-β-cyclodextrin concentration | | | | |
| ingredient | stereochemistry | 0% | 2.5% | 5% | 7.5% | 10% |
| | cis (mixture of 4 isomers) saperconazole | n.d. | 0.97 | 4.62 | 8.92 | 16.92 |
| 5 | (−)-[2S-[2a,4a,4(S)]] | n.d. | 1.60 | 6.23 | 15.34 | 28.52 |
| 6 | (−)-[2S-[2a,4a,4(R)]] | n.d. | 1.13 | 5.05 | 13.42 | 26.51 |
| 7 | (+)-[2R-[2a,4a,4(R)]] | n.d. | 1.78 | 7.91 | 19.94 | 39.31 |
| 8 | (+)-[2R-[2a,4a,4(S)]] | n.d. | 2.02 | 8.15 | 18.14 | 36.31 | n.d.: not detectable by U.V. spectrometry

EXAMPLE 17

The solubility of compound 3 in artificial gastric juice was compared to that of itraconazole. About 10 mg of either product was added to 100 ml artificial gastric juice (0.2 g NaCl+0.7 ml concentrated HCl diluted to 100 ml) at ambient temperature. The mixture was stirred and a sample was taken from each solution at regular intervals. The amount of dissolved active ingredient was determined following the procedure described in the previous example. The dissolved amount of each ingredient (in mg/100 ml) is summarized in the table below.

| Time | concentration of dissolved itraconazole | concentration of dissolved compound 3 |
|---|---|---|
| 5 min. | n.d. | 0.005 |
| 15 min. | n.d. | 0.037 |
| 30 min. | n.d. | 0.15 |
| 1 h. | 0.023 | 0.32 |

-continued

| Time | concentration of dissolved itraconazole | concentration of dissolved compound 3 |
|---|---|---|
| 2 h. | 0.079 | 0.69 |
| 3 h. | 0.15 | 1.09 |
| 4 h. | 0.19 | 1.41 |
| 6 h. | 0.27 | 1.94 |
| 26 h. | 0.40 | 3.93 |
| 46 h. | 0.40 | 5.08 |
| 51 h. | 0.41 | 5.39 |
| 69 h. | 0.45 | 6.36 | n.d.: not detectable by U.V. spectrometry

We claim:

1. A pharmaceutical antifungal composition comprising a pharmaceutically acceptable carrier and a therapeutically effective amount of at least one stereoisomeric form of itraconazole that has a stereoisomeric purity of at least 96% and is:
   (+)-[2R-[2α,4α,4(R)]]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one; or
   (+)-[2R-[2α,4α,4(S)]]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one; or
   a pharmaceutically acceptable acid addition salt form thereof.

2. The composition according to claim 1 wherein said composition is adapted for oral administration.

3. The composition according to claim 1 adapted for parenteral delivery.

4. The composition according to claim 3 adapted for intramuscular delivery.

5. The composition according to claim 3 adapted for topical delivery.

6. An anti-infective composition for the treatment of a human in need of therapy for a systemic or topical fungal infection which comprises a pharmaceutically acceptable carrier and a therapeutically effective amount of (2R,4S) itraconazole or a pharmaceutically acceptable salt thereof, substantially free of its (2S,4R) stereoisomer.

7. The composition according to claim 6 wherein said composition is adapted for oral administration.

8. The composition according to claim 6 adapted for parenteral delivery.

9. The composition according to claim 8 adapted for intramuscular delivery.

10. The composition according to claim 6 adapted for topical delivery.

11. A method for treating fungal infections in a human which comprises administering to a human a therapeutically effective amount of at least one stereoisomeric form of itraconazole that has a stereoisomeric purity of at least 96% and is:
    (+)-[2R-[2α,4α,4(R)]]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one; or
    (+)-[2R-[2α,4α,4(S)]]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one; or
    a pharmaceutically acceptable acid addition salt form thereof.

12. A method for treating local and systemic fungal infections in a human which comprises administering to a human, in need of antiinfective therapy, an amount of (2R,4S) itraconazole, or a pharmaceutically acceptable salt thereof, substantially free of its (2S,4R) stereoisomer, said amount being sufficient to alleviate said infections.

13. A stereoisomeric form of itraconazole (X=Cl) having the formula cis-(I)

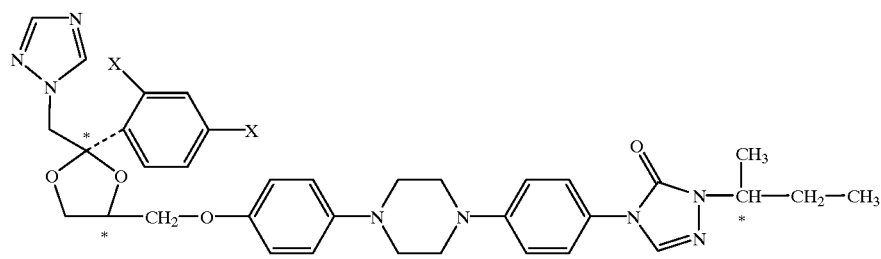

or a pharmaceutically acceptable acid addition salt form thereof, wherein the (1H-1,2,4-triazol-1-ylmethyl) moiety and the substituted phenoxy moiety are located at the same side of the plane defined by the 1,3-dioxolane ring and said stereoisomeric form has a stereoisomeric purity of at least 96%, which form is:
   (+)-[2R-[2α,4α,4(R)]]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one; or
   (+)-[2R-[2α,4α,4(S)]]-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one.

* * * * *

UNITED STATES PATENT AND TRADEMARK OFFICE
CERTIFICATE OF CORRECTION

PATENT NO. : 5,998,413
DATED : December 7, 1999
INVENTOR(S) : Heeres et al.

It is certified that error appears in the above-identified patent and that said Letters Patent is hereby corrected as shown below:

Column 4,
Line 58, please delete "dihrxybutanedioic" and insert therefor -- dihydroxybutanedioic --;

Column 7,
Line 54, please insert -- (+)-(S)-(VII) can be obtained similarly with (S)-camphor sulfonic acid from racemic (±)-(VII), or preferably from the mother liquors of the previous resolution step with -- after the words "sulfonic acid;";
Line 59, please delete "anylose" and insert therefor -- amylose --;

Column 8,
Line 46, please delete "(R)-1,3 dihydroxypropyl" and insert therefor -- (R)-1,2,-dihydroxypropyl --;

Column 11,
Line 24, please delete "bydroxypropyl" and insert therefor -- hydroxypropyl --;
Line 40, please delete "Shaardinger" and insert therefor -- Shardinger --;

Column 12,
Line 32, please delete "deleterious effect" and insert therefor -- additives of any --;

Column 15,
Line 22, please delete "while" and insert therefor -- whole --;
Line 40, please delete "C:" and insert therefor -- C; --

Column 16,
Line 50, please delete "(365 mm)" and insert therefor -- (365nm) --;
Line 52, please delete "(365 mm)" and insert therefor -- (365nm) --;

UNITED STATES PATENT AND TRADEMARK OFFICE
CERTIFICATE OF CORRECTION

PATENT NO.    : 5,998,413
DATED         : December 7, 1999
INVENTOR(S)   : Heeres et al.

It is certified that error appears in the above-identified patent and that said Letters Patent is hereby corrected as shown below:

Column 17,
Line 48, please delete "phenol" and insert therefor -- phenyl --;
Line 51, please delete "13.46" and insert therefor -- 18.78 --;
Line 59, please delete "(+)-(S)" and insert therefor -- (-)-(R) ---;

Signed and Sealed this

Eighteenth Day of June, 2002

Attest:

Attesting Officer

JAMES E. ROGAN
*Director of the United States Patent and Trademark Office*